United States Patent [19]

Liang

[11] Patent Number: 5,827,658
[45] Date of Patent: Oct. 27, 1998

[54] ISOLATION OF AMPLIFIED GENES VIA CDNA SUBTRACTIVE HYBRIDIZATION

[75] Inventor: Bertrand C. Liang, Silver Spring, Md.

[73] Assignee: The United States of America as reprsented by the Department of Health and Human Services, Washington, D.C.

[21] Appl. No.: 700,763

[22] Filed: Aug. 9, 1996

[51] Int. Cl.$^6$ .............................. C12Q 1/68; C12P 19/34
[52] U.S. Cl. ............................................... 435/6; 435/91.2
[58] Field of Search ....................................... 435/6, 91.2

[56] References Cited

FOREIGN PATENT DOCUMENTS

| | | |
|---|---|---|
| 518650 | 12/1992 | European Pat. Off. . |
| 622457 | 11/1994 | European Pat. Off. . |
| WO 89/12695 | 12/1989 | WIPO . |
| WO 94/11383 | 5/1994 | WIPO . |

OTHER PUBLICATIONS

Weiland et al, PNAS 87: 2720–2724, 1990.
Fargnoli et al, Anal. Bioch. 187: 364—373, 1990.
Schweinfest et al, Genet Annal Tech. 7: 64–70, 1990.
92–171651 Abstract, Derwent Publications Ltd., London, GB; Shin (Apr. 9, 1992).
Liang et al. "Mitochondrial DNA copy number changes in human gliomas", *Cancer Letters* 105: 167–173 (1996).
Ace et al. "Isolation of Progesterone–Dependent Complementary Deoxyribonucleic Acid Fragments from Rhesus Monkey . . . ", *Endocrinology* 134(3): 1305–1309 (1994).
Hurtt et al "Amplification of Epidermal Growth factor Receptor Gene in Gliomas: Histopathology and Prognosis" vol. 51.
Brodeur et al Molecular Basis of Clinical Heterogeneity in Neuroblastoma, *Oncology* 14(2): pp. 111–116, 1992. No. 1.
Liang et al. Gene Amplification Elucidated by Combined Chromosomal Microdissection and Comparative Genomic.
Fukomoto et al "Detection of Amplified Sequences in Mammalian DNA by In–Gel Renaturation and SINE Hybridization" *Somatic*.
Hayashizaki et al "Restriction landmark genomic scanning method and its various applications" *Electrophoresis* 1993, 14, pp.
Liang et al. "Distribution and cloning of eukaryotic mRNA's by means of differential display: refinements and optimization".
Ace et al Isolation of Progesterone–Dependent Complementary Deoxyribonucleic Acid Fragments from Rhesus Monkey Lisitsyn et al "Cloning the Differences Between Two Complex Genomes" *Science* vol. 259, (Feb. 12, 1993).
Collins "Amplified genes in human gliomas", *Cancer Biology*, vol. 4, 1993: pp. 27–32.
Hurtt et al. "Amplification of Epidermal Growth factor Receptor Gene in Gliomas: Histopathology and Prognosis," *J. Neuropathol Exp Neurol* vol. 51 (1): 84–90 (1992).
Brodeur et al. "Molecular Basis of Clinical Heterogeneity in Neuroblastoma," *Am J Pediatr Hematol Oncol* (US) 14(2).
Liang et al. "Gene Amplification Elucidated by Combined Chromosomal Microdissection and Comparative Genomic Hybridization," *Cancer Genetics and Cytogenetics* 80(1): 55–59 (1995).
Fukomoto et al. "Detection of Amplified Sequences in Mammalian DNA by In–Gel Renaturation and SINE Hybridization," *Somatic Cell Mol Genet* 12(6): 611–24 (1986).
Hayashizaki et al. "Restriction landmark genomic scanning method and its various applications," *Electrophoresis* 14(4): 251–258. (1993).
Liang et al. "Distribution and cloning of eukaryotic mRNAs by means of differential display: refinements and optimization," *Nucleic Acids Research* 21(14): 3269–3275 (1993).
Ace et al. "Isolation of Progesterone–Department Complementary Deoxyribonucleic Acid Fragments from Rhesus Monkey Edometrium by Sequential Subtractive Hybridization and Polymerase Chain Reaction Amplification," *Endocrinology* 134(3): 1305–1309 (1994).
Lisitsyn et al. "Cloning the Differences Between Two Complex Genomes," *Science* 259: 946–51 (1993).
Collins "Amplified genes in human gliomas," *Semin Cancer Biol.* (*US*) 4(1) 27–32 (1993).
Su et al. "Direct Isolation of Genes Encoded Within a Homogenously Staining Region by Chromasome . . . " *PNAS* 91:9121–25 (1994).

*Primary Examiner*—Eggerton A. Campbell
*Attorney, Agent, or Firm*—Spencer & Frank

[57] ABSTRACT

A method of analyzing an amplified gene, including determining its copy number, involves subtractive hybridization of two cDNA libraries, one from the tissue of interest and the other containing biotinylated cDNA from normal tissue, where the annealed cDNA is removed by means of magnetic beads coated with streptavidin or avidin. The cDNA isolated after subtractive hybridization represents amplified DNA, and it is analyzed to determine what gene(s) were amplified. Furthermore, the copy number of the gene(s) can be estimated. The copy number thus determined can be correlated to the severity of a pathogenic state, to its prognosis, or to treatment efficacy.

7 Claims, No Drawings

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO:1:

GAGTAGAATT CTAATATCTC                               20

( 2 ) INFORMATION FOR SEQ ID NO:2:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO:2:

GAGATATTAG AATTCTACTC                               20

ISOLATION OF AMPLIFIED GENES VIA CDNA SUBTRACTIVE HYBRIDIZATION

BACKGROUND OF THE INVENTION

Gene amplification has been noted during development, and also is an important phenomena in the pathogenies of malignancy. In particular, gene amplification has been well-documented in tumors.

Most if not all tumor types have been shown to be capable of overexpressing certain genes, which has been thought to represent an intermediate event in the multistep pathway to tumorigenesis. Alitalo and Schwab, *Adv. Canc. Res.* 47: 235–81 (1986), and GENE AMPLIFICATION IN MAMMALIAN CELLS: A COMPREHENSIVE GUIDE, Kellems ed. (Marcel Dekker, Inc. 1993). This phenomenon most likely represents one of several ways the cell uses to activate genes which effect abnormal, unregulated, growth.

Gene amplification of a variety of genes has been found, whose function span all aspects of cellular machinery. Westermark et al. in NEURO-ONCOLOGY: PRIMARY MALIGNANT BRAIN TUMORS, Thomas ed. (Johns Hopkins Univ. Press 1990). But the collection of amplified genes described to date is far from complete. Indeed, in a recent study of specimens from tumorigenic tissue with cytologic evidence of gene amplification, the genes amplified were not known genes. Saint-Ruf et al., *Genes. Chrom. Canc.* 2:18–26 (1990). The identification of genes with increased copy number are important, since they will aid in the understanding of the biology of these neoplasms, and to a certain extent may reflect the aggressiveness of the tumor and give an indication of prognosis. Furthermore, it may be possible to use copy information to determine if treatment is effective in arrest of disease development. Indeed, for example, the presence of gene amplification in neuroblastoma and glioma portend to a worsened patient prognosis. Hurtt et al., *J. Neuropath. Exp. Neuro.* 51: 84–90 (1992), and Brodeur & Nakagawara, *Am. J. Pedaitr. Hematol. Oncol.* 14: 111–16 (1992).

As a result, sensitive methods which identify amplified genes in tumor specimens would be of interest in studying the pathogenesis of malignancy. Several techniques have been used in the past to assess gene amplification. Some of these techniques combine a cytogenetic assessment with a positional cloning and physical isolation approach, resulting in first order clones from a region. Su, et al. *Proc. Nat'l Acad. Sci. USA* 91: 9121–25 (1994), and Liang et al., *Canc. Genet. Cytogenet.* 80: 55–59 (1995). Other approaches utilize the visualization of renatured DNA to detect increase in gene copy number. Fukumoto & Robinson, *Somat. Cell & Mol. Genet.* 12: 611–23 (1986), and Hayashizaki et al., *Electrophoresis* 14: 251–58 (1993). For these methods to work, the amplicon (the amplified region) must be large enough to be seen on a cytologic scale, or they require significant amplification of genes (>10–15 copies). Furthermore, they are fairly labor intensive, require specialized equipment, or investigate only one genetic region for amplified genes in a given tumor. A method which is simple, does not require specialized equipment or prior knowledge of the genomic state of the tumor sample, and is sensitive to lower levels of increased copy number, would be valuable to assess gene amplification.

The present invention provides a more sensitive method of identifying cDNAs representing amplified genes and a way of estimating their copy number. The method employs subtractive hybridization against a varying amount of biotinylated subtractor cDNA from normal tissue, and calls for removal of annealed cDNA by trapping it on magnetic spheres coated with streptavidin/avidin to trap biotinylated DNA.

Approaches are described in the literature which identify mRNA expressed differentially, either in only some cell types, or at certain times of a biological process, or during infection by a parasite or a virus, etc., but not to identify amplified genes. Those studies generally employ subtractive hybridization to reveal the differentially expressed mRNA (s). In one such approach, Liang and colleagues have used the anchored-end technique to look for specific differences in mRNA populations. Liang et al., *Nucleic Acids Res.* 21: 3269–75 (1993). The Liang method, called "differential display," employs a decanucleotide of arbitrary sequence as a primer for PCR, internal to the mRNA, and a polyTMN primer on the 3'-end of mRNAs; "M" in this context is randomly G,C or A, but N is chosen as one of the four possible nucleotides.

When such sets of primers are employed, patterns of cDNAs can be visualized upon polyacrylamide gel electrophoresis of the PCR product, and the comparison of such patterns produced by mRNAs from two sources reveal the differentially expressed mRNAs. The differential display method can indicate individual, differently expressed mRNAs, but cannot constitute a complete library of such mRNAs. Furthermore, the method is not suited to detect genes expressed in both tissues that differ only in the amount of transcription. Moreover, if the individual cDNA candidates are desired for further analysis, they would require recovery from the gel and subcloning, which would add effort and expense.

Another method for identification of differentially expressed genes was reported. Ace et al., *Endocrinology* 134: 1305–09 (1994). This method is directed toward identification of inducible genes, as was the case with the above-mentioned Liang technique. It must use very high levels of biotinylated cDNA to subtract background cDNA. The biotinylated cDNA is removed by mixing with streptavidin and phenol:chloroform extraction.

Lisitsyn et al., *Science* 259: 946–51 (1993), have described a representational differences analysis (RDA) which uses subtractive hybridization and PCR technology to define the differences between two genomes. Like other subtractive hybridization protocols, in RDA there are defined two sets of DNAs, the "tester" DNA and the "driver" DNA. According to the RDA protocol, the DNA of the two genomes to be compared are digested by restriction endonucleases, and a dephoshorylated double-stranded oligonucleotide adapter is ligated. After denaturation and hybridization of driver and tester DNA, oligonucleotides from the adopters covalently linked to tester DNA were used to amplify unique DNA sequences of tester library. The adapters are partially double-stranded DNAs made by partially complementary oligos, where the single-stranded sequence at one end of the double stranded adapter is complementary to the single-strand tail of the digested genomic DNA.

The combined use of (i) restriction enzyme-digested DNA as PCR substrate and (ii) the preferential amplification of shorter substrates results in a population of fairly short, amplified DNA molecules. The adapters then are removed by cleavage with the restriction enzymes used originally to digest the DNA. To the tester DNA, new adapters with novel sequences are ligated, the tester and driver DNA are mixed, the DNA strands are separated by heating ("melting"), and the DNA's are cooled to allow for reannealing. PCR is performed with primers complementary to the adapters on tester DNA, thereby amplifying only target DNA, i.e., only DNA unique to the tester DNA. By restriction enzyme digestion of the adapters from the amplified DNA and ligation of additional, novel adapters, followed by PCR, the target DNA is amplified to become the dominant fraction. The RDA procedure does not use any physical method of separation between the tester and driver DNA which, if used, would allow enhanced purification of target DNA. The method is used only to identify differences between genomes, and was not used to identify differential cDNA expression.

Methods that employ streptavidin to bind biotinylated DNA and use of coated magnetic particles are well known. Such coated particles are available commercially.

SUMMARY OF THE INVENTION

The present invention relates to a simple method for isolating any amplified gene from a tissue, and for estimating its copy number. The methodology of the invention uses subtractive hybridization with limited excess of biotinylated cDNA derived from normal tissue. According to the method, cDNA prepared from a tissue of interest is annealed to biotinylated cDNA prepared from normal tissue. Use of magnetic beads coated with streptavidin or avidin allows the convenient and efficient removal of biotinylated cDNA, and the remaining fraction is highly enriched for such cDNA from the tissue of interest that represents amplified genes. The cDNA thus obtained can be analyzed to identify the amplified gene. Novel amplified genes would be discovered with this method. Furthermore, an estimate of copy number of an amplified gene can be made. Estimates of copy number are of interest in as far as they could be correlated to aggressiveness of a malignancy, prognosis, and potentially to effectiveness of treatment to arrest disease development.

According to one aspect of the present invention, therefore, a method is provided for analyzing an amplified gene in a first tissue sample, which method comprises of the steps of: (a) providing cDNA derived from mRNA from said sample; (b) annealing said cDNA to biotinylated cDNA, wherein said biotinylated cDNA was prepared from mRNA from a sample of normal tissue, and is sufficiently in excess to hybridize most copies of cDNA derived from non-amplified genes of said tissue of interest; (c) removing said annealed cDNA by binding to magnetic beads coated with streptavidin or avidin; (d) amplifying cDNA not removed in step (c) by PCR; and then (e) analyzing copies of cDNA that were not annealed and removed by binding to said magnetic beads. For example, the first tissue involved can be a tumor tissue, and the biotinylated cDNA can be prepared from a normal tissue.

In a preferred embodiment, the method further comprises a step, after step (a) and before step (b), of attaching an adapter oligo, constructed by two complementary oligonucleotides, to the ends of said cDNA. Two such oligonucleotides that are preferred in this context are (SEQ ID NO:1) 5'-GAGTAGAATTCTAATATCTC-3' and (SEQ ID NO:2) 5'-GAGATATTAGAATTCTACTC-3'. In another preferred embodiment, the analysis conducted in step (e) includes the use of clones derived from said cDNA to hybridize to DNA or to mRNA from said first tissue sample and to DNA or mRNA from said sample from normal tissue, respectively, so as to verify that said isolated cDNA is from an amplified gene and to ascertain copy number.

DETAILED DESCRIPTION OF THE PREFERRED EMBODIMENTS

The present invention provides a method for isolation of amplified genes which allows for estimation of copy number of an amplified gene. The method can identify amplified gene(s) from any tissue of interest, where tissue of interest is defined as any tissue/cell/organ where gene amplification is suspected, such as tissue that appears malignant. In a preferred embodiment, therfore, amplified genes are isolated from tumorigenic tissue.

The method entails substantive hybridization of two sets of cDNA, one provided from the tissue of interest and the other from normal tissue, i.e., where amplification is not expected, relative to the tissue of interest. For example, the cDNA from the tissue of interest would be from a tumor of a human patient and the normal cDNA would be from normal tissue.

The technique applied to produce the cDNA sets is not critical to the present invention. Any of the known methods of purifying total RNA or mRNA and usage of any of the known primers and methods are compatible with the current invention. For example, but not limited to those examples, primers for first strand synthesis can include polyT, "anchored" polyT, primers with restriction enzyme recognition sequences build-in, primers to complement a polyN tail created by the terminal transferase, where N stands for any one of the four nucleotides to be used. The polymerases can be any of the available and known polymerases. Either set of cDNAs could be maintained and amplified by cloning into a plasmid. A set of cDNAs from the normal tissue can serve as subtractor cDNA for annealing to cDNA from samples from multiple tissues of interest. Further variations and options would be readily apparent to one skilled in the art.

In a preferred embodiment, a double stranded adapter oligo is attached to the ends of the cDNA set prepared from the tissue of interest. The oligo set is composed of two, at least partially complementary synthetic oligos. They are attached to the cDNA by a DNA ligase. The attachment can be preceded by creation of protruding ends on the cDNA by cleavage with a restriction endonuclease for which a recognition side was built-in on the cDNA ends by the choice of oligos used to create the cDNA set. In this embodiment, the oligo set to be attached is designed to create, after self annealing, complementary ends to the cDNA. Alternatively, the cDNA is made blunt-ended by enzymatic reaction, Klenow fragment by example. Then the oligo set would be ligated to the cDNA by a blunt-ended ligation.

In a preferred embodiment, the cDNA ends are made blunt-ended as described above and ligated to an adapter set which is blunt ended at least at one end. In another preferred embodiment, the oligonucleotides that make up the adopter set are A (SEQ ID NO:1): 5'-GAGTAGAATTCTAATATCTC-3' and B: 5'-GAGATATTAGAATTCTACTC-3'.

An important feature of the present invention is that the cDNA derived from the normal tissue is biotinylated. Again, this requirement can be achieved by any of a number of methods readily apparent to one skilled in the art. By way of example, but not limited to those examples, the biotin label can be incorporated into the cDNA starting with the synthesis of a second strand or can result from PCR amplification of a pre-made cDNA set. The label can also be introduced by PCR amplification or by "nick-translation" of a cDNA set or by photobiotinylation.

The invention also includes a mixing of the two cDNA sets, derived from the tissue of interest and from the normal tissues, followed by denaturation and annealing. Critical in this process is the ratio of cDNA from tissue of interest to cDNA from normal tissue (subtractor cDNA). An excess of subtractor cDNA will increase the efficiency of annealing (and eventual removal, see below) of the sequences that are common to the two cDNA sets and are not amplified in the tissue of interest. On the other side, if amplification is small and leads to a small gene copy number, great excess of subtractor cDNA will anneal and remove also the amplified copies of cDNA from the tissue of interest. In practice, in a preferred embodiment, if the degree of amplification is not known or estimated from independent means, a few ratios of cDNA (interest/normal) would be used, from 1/2 to 1/15. The melting and annealing conditions are standard for such experiments and known to one skilled in the art. The annealing results in populations of hybrid cDNAs.

Another critical step of the current invention is the use of magnetic beads coated with either streptavidin or avidin to remove DNA containing biotin. Other researchers use streptavidin for binding biotin labeled DNA, followed by phenol:chloroform extractions. Magnetic spheres make the job of removal of biotin containing DNA easier, safer and more thorough. Thus, little biotin labeled DNA should escape untrapped, reducing the background levels of cDNA recovered from the subtractive hybridization. Streptavidin coated beads are available commercially. They are used by other to remove biotin labeled DNA, unlike the current disclosure that employs them within in a subtractive hybridization protocol.

The subtractive hybridization results in a cDNA fraction, hereafter called flow-through, enriched in cDNAs representing amplified genes, but not free of all other cDNAs. Initial analysis is sometimes facilitated by cloning the cDNAs of the flow-through. The cloning step itself is facilitated by first carrying out a PCR amplification of the flow-through cDNAs. Both of these steps can be accomplished by use of the previously described adapter set that can a) contain a restriction enzyme recognition site and b) one of the oligos in the set can be used as PCR primer. In specific cases, the tissue of interest may be suspected to have some known gene amplified. Under specific circumstances this could be determined experimentally by direct dideoxy sequencing of the flow-through fraction, without cloning of the cDNAs, if the fraction is highly enriched for some unique gene sequence and the sequencing/first-strand-cDNA-synthesis-primer is sitting at a unique site on the cDNA molecule. If cloning is carried out to facilitate further analysis, it would next allow the choosing of one, or a limited number of clones, for sequencing and as a probe (see also below). Choosing the clone/clones can be easily accomplished by determining insert size, a limited restriction map, or by hybridization between clone inserts, to determine the desired clone. All these analysis employ standard molecular biology techniques and numerous options and shortcuts will be readily apparent to one skilled in the art. In either or both case, cloned flow-through cDNAs or direct sequencing, "single lane" dideoxy sequencing may suffice if the sequence is known. Sequencing reactions could employ as primer the same oligo described above as part of the oligo set.

Another analysis would be either a southern or a northern experiment. The chosen cloned cDNA(s) described above would be hybridized to equivalent amounts of nucleic acids, DNA and/or RNA, from both the tissue of interest and the normal tissue. The relative intensity of the bands would be compared spectrophotometrically and result in a estimate of copy number. To a person skilled in the art, variations and shortcuts will be readily apparent. For example, but not limited to this examples, one could use dot blots rather than gels and blotting, or one can incorporate a control hybridization with a probe not expected to hybridize to amplified genes, to standardize the amount of nucleic acids from the two tissues used. As stated in the Summary of the Invention, copy number and copy number changes can be used as indication of the state of the malignancy, prognosis, and to confirm a possible arrest of disease progress in response to treatment.

The following commentary describes an illustrative example of successful isolation of three amplified genes, one of them a novel gene, via the present invention. The copy number was determined to be seven, thirteen, and sixteen. This description does not imply that the invention is limited with respect to the experimental techniques or the tissues used, or in any other way.

Production of cDNAs

Messenger RNA was extracted from tumor cell lines by standard techniques. First strand cDNA synthesis was carried out using the RiboClone kit (Promega, Madison, Wis.) using random primers and AMV reverse transcriptase according to the manufacturers instructions. Second strand synthesis was performed using the same kit, with incubation times >4 hours to produce cDNAs >3 kb. The cDNAs were phenol/chloroform extracted, ethanol precipitated and resuspended in TE buffer. These were then blunt ended with the Klenow fragment of DNA polymerase I, and linkers were attached (A (SEQ ID NO:1): 5'-GAGTAGAATTCTAATATCTC-3'; B (SEQ ID NO:2): 5'-GAGATATTAGAATTCTACTC-3'). Cleavage of linkers ligated to themselves was accomplished by digesting the reaction product with XhoI. To obtain cDNA product for hybridization, PCR was performed with 1.5 $\mu$M linker A in 50 $\mu$l reaction volume, using 40 ng of template DNA, 200 $\mu$M each dNTP, 2 Mm MgCl$_2$, 50 Mm KCl, 10 Mm Tris Hcl (pH 8.4), 0.1 mg/ml gelatin, 1 Unit of Taq polymerase. Cycling conditions were: 95° C.×5 minutes, followed by 30 cycles of 94° C.×1 minute, 72° C.×2 minutes, with a final extension of 72° C.×5 minutes. PCR products were concentrated with Centricon 30 filters (Beverly, Mass.) and ethanol precipitated.

A normal brain cDNA library with T3 and T7 promotor sequences flanking the insert was purchased from Stratagene (La Jolla, Calif.). The library was phenol:chloroform extracted, ethanol precipitated, and resuspended in TE buffer. Biotinylation of the normal brain cDNAs was performed by PCR as follows. In a 50 $\mu$l reaction volume, 100 ng of template cDNA, 1.2 $\mu$M T3 and T7 promoter primers, 200 $\mu$M each dNTP, 2 mM MgCl$_2$, 50 mM KCl, 10 mM Tris HCl (pH 8.4), 0.1 mg/ml gelatin, 1 Unit of Taq polymerase, and 100 $\mu$M biotin-16-dUTP (Boehringer Mannheim, Indianapolis, Ind.) were combined and cycled at 95° C.×5 minutes, followed by 30 cycles of 94° C.×1 minute, 56° C.×1 minute, 72° C.×2 minutes, with a final extension of 72° C.×5 minutes. These PCR products were filtered and ethanol precipitated as noted previously.

Cell Lines

The cell lines HL60 and A431 were obtained from the American Type Tissue Collection (ATCC; Rockville, Md.). HL60 harbors amplification of the c-myc gene, while A431 shows erb-b amplification. HL60 was maintained in RPMI with 20% fetal bovine serum supplemented with penicillin-streptomycin (10,000 U), with A431 kept in Dulbecco's modified Eagle's medium with 4.5 g/L glucose, 10% fetal bovine serum, and 10,000 U penicillin-streptomycin. An established glioma cell line, PFAT-MT, was a generous gift of Dr. Dan Fults (University of Utah), and was derived from a patient with a glioblastoma multiform. The line was grown in RPMI media supplemented with 10% fetal bovine serum.

cDNA Hybridization

Tumor cDNAs were subtracted by hybridization with biotinylated normal brain cDNAs. Tumor cDNA (1 μg) was combined with 5 μg (A431) and 10 μg (HL60, PFAT-MT) of biotinylated normal brain cDNA, and ethanol precipitated. The pellet then was resuspended in a hybridization solution consisting of 0.1M PIPES (pH 6.8), 1.2M NaCl, 2M EDTA, and 0.2% SDS, with an equal amount of formamide subsequently added. The solution was heated to 95° C.×1 minute, and hybridized at 42° C.×36–48 hours. 90 μl of buffer (10 mM Tris HCl, pH 7.5, 1 mM EDTA, and 2M NaCl) was added and combined with 200 μg of streptavidin coated magnetic beads (Dynal Inc., Lake Success, N.Y.) prepared according to the manufacturers instructions. This was gently agitated for 30 minutes on a rotating platform, and subsequently placed into a magnet, with the supernatant removed to another tube. 100 μl of buffer was again added, repeating the previous step. The supernatant was concentrated and ethanol-precipitated as described. PCR then was performed with linker A as noted above, with a prolonged extension step of 8 minutes, to obtain cDNA for future cloning experiments.

PCR Product Cloning

PCR products were cloned into plasmids using the TA cloning kit (Invitrogen, San Diego, Calif.) according to the manufacturers instructions. Individual colonies were picked and grown using standard protocols and underwent PCR with linker A as above to determine insert size.

Nucleic Acid Hybridization

DNA extraction, Southern and northern transfers and hybridizations were performed using standard methods with minor modifications. Typically 10 μg of DNA and 5 μg of mRNA were used for Southern and northern hybridizations, respectively. TaqI was used to digest DNA. The erb-b pE7 probe was obtained from the ATCC; the 3rd exon of c-myc was purchased from Oncor (Gaithersburg, Md.). Densitometric analysis was performed by digitizing autoradiographs with a Sony SC-77 camera (Cypress, Calif.) linked to a Scion LG-3 video frame grabber (Frederick, Md.) via a Macintosh II computer (Cupertino, Calif.). Images were captured with the program NIH-Image (version 1.55) at 8 bit data and utilized as uncompressed TIFF files. Measurements were normalized to a single copy control probe (β-actin) prior to calculating the degree of amplification.

Sequencing Reactions

Dideoxy chain-termination sequencing was performed by the method of Sanger, using a modified cycle sequencing kit (Life Technologies, Gaithersburg, Md.). Primers used included both T7 and Sp6 promoter sequences on plasmid templates derived as described above.

PCR Results from cDNAs

Linkers designated "A" and "B" were attached to the tumor cDNAs and used as primers for PCR. A normal brain cDNA library with T3 and T7 promotor sequences flanking the insert was obtained, and underwent PCR in the presence of biotin-16-dUTP. Upon gel electrophoresis, a smear of products was found between several hundred base pairs to over 2 kb. For cell lines A431 and HL60 typical PCR reaction volumes were 150–200 μl to obtain several micrograms of product for later hybridization. The biotinylated brain cDNAs required 500–600 μl of total reaction volume to generate 10 μg of product to be used for hybridization. In each case all tubes showed the same sized smear.

Results of cDNA Extraction

The tumor cDNA and normal brain cDNA library products from PCR were then added together and ethanol precipitated in preparation for the extraction. After the addition of hybridization buffer and hybridization of the tumor cDNAs with excess biotinylated normal brain cDNAs, streptavidin-coated magnetic beads were used to remove the hybridized product; this, since streptavidin binds biotin essentially irreversibly. To assess the ability to titrate amplification detection, the A431 cell line, which shows approximately 7-fold amplification of erb-b was hybridized with 5-fold excess normal brain cDNAs, and the HL60 cell line, which was found to have a copy number of approximately 13, was hybridized with 10-fold excess normal brain cDNAs. It was estimated that this would leave excess tumor cDNA sequences which were over and above the stated excess normal brain cDNAs. These products were isolated by precipitation, and PCR with linker A (the flanking sequence of the tumor cDNAs) was performed. Again a smear was noted, in a range of several hundred base pairs to over 2 kb in both HL60 and A431 cell lines. These products were directly cloned into plasmids for further analysis.

Cloning of Extracted cDNAs

The cDNAs which were extracted and recovered by PCR were cloned into plasmids which subsequently underwent PCR to obtain information about the presence and size of inserts, as well as for later use as probes. Plasmids were also used as templates for sequencing reactions. Inserts were of various sizes, with most being smaller than 1 kb in length. This result was expected given the bias of the cloning system utilized for more efficient cloning of smaller inserts. Greater than 90% of clones showed inserts when evaluated by PCR.

Identity of Partially Sequenced Clones

Ten clones from each extraction from A431 and HL60 were partially sequenced to determine if the known oncogene was detected. From the HL60 extraction where a 10-fold excess concentration of normal cDNAs was used, c-myc sequences were found in 6/12 clones. Among the other sequences, two contained Alu sequences. The A431 clones which were derived from the 5-fold normal brain cDNA extraction showed 5/12 sequences of erb-b. Several of these clones also had Alu repeats present.

Results of Extraction From a Glioma Cell Line

Extraction using cDNAs derived from a high grade glioma cell line was performed to assess the ability to isolate amplified cDNAs from an uncharacterized source. A 10-fold excess of normal brain cDNAs was used. cDNAs were obtained and processed as described for the tumor cell lines, with extraction, PCR and cloning performed as noted. Probes were obtained for Southern analysis. We initially assessed for the presence of erb-b amplification, since this has been considered the most frequently amplified gene in gliomas. Collins, *Seminars Canc. Biol.* 4: 27–32 (1993). No evidence of amplification was noted when compared to normal brain DNA. Hybridization then was performed using clones from the extraction. There was dramatic hybridization of the probe to the tumor lane from which the clone was extracted when compared to the adjacent normal brain DNA. Densitometric analysis showed copy number of approximately 16 when normalized to a single copy control (β-actin). Preliminary data did not reveal this clone to be a known oncogene sequence.

What is claimed is:

1. A method for analyzing an amplified gene in a first sample, comprising of the steps of:

(a) providing cDNA derived from mRNA from said sample;

(b) annealing said cDNA to biotinylated cDNA, wherein said biotinylated cDNA was prepared from mRNA from a sample of normal tissue, and is in excess from about 2 to about 15 fold over the cDNA so as to hybridize most copies of cDNA derived from non-amplified genes of said tissue of interest;

(c) removing said annealed cDNA by binding to magnetic beads coated with streptavidin or avidin;

(d) amplifying cDNA not removed in step (c) by PCR;

(e) verifying that all non-hybridized, amplified cDNA obtained in step (d) is from an amplified gene; and then (f) analyzing copies of cDNA obtained in step (e).

2. The method of claim 1, wherein said first tissue sample is from a tumor, and said biotinylated cDNA is prepared from a normal tissue.

3. The method of claim 1, further comprising a step, after step (a) and before step (b), of attaching an adapter oligo, constructed by two complementary oligonucleotides, to the ends of said cDNA.

4. The method of claim 3, where said complementary oligonucleotides are A: 5'-GAGTAGAATTCTAATATCTC-3' SEQ ID NO:1 and B: 5'-GAGATATTAGAATTCTACTC-3' SEQ ID NO:2.

5. The method of claim 1, wherein said analysis in step (e) includes sequencing of said cDNA.

6. The method of claim 1, wherein said analysis in step (e) includes use of clones derived from said cDNA to hybridize to DNA or to mRNA from said sample and to DNA or mRNA from from normal tissue, respectively, so as to verify that said isolated cDNA is from an amplified gene and to ascertain copy number.

7. The method of claim 1, wherein the amount of said biotinylated cDNA is adjusted empirically.

* * * * *